US 6,737,534 B2

(12) United States Patent
Pontiroli et al.

(10) Patent No.: US 6,737,534 B2
(45) Date of Patent: May 18, 2004

(54) PROCESS FOR THE PREPARATION OF TAXAN DERIVATIVES

(75) Inventors: Alessandro Pontiroli, Milan (IT); Ezio Bombardelli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/432,728

(22) PCT Filed: Nov. 22, 2001

(86) PCT No.: PCT/EP01/13614
§ 371 (c)(1),
(2), (4) Date: May 27, 2003

(87) PCT Pub. No.: WO02/44161
PCT Pub. Date: Jun. 6, 2002

(65) Prior Publication Data
US 2004/0030164 A1 Feb. 12, 2004

(30) Foreign Application Priority Data
Nov. 28, 2000 (IT) ..................................... MI2000A2553

(51) Int. Cl.$^7$ .................... C07D 317/70; C07D 407/02; C07D 493/12
(52) U.S. Cl. ........................................ 549/296; 549/297
(58) Field of Search ................................. 549/296, 297

(56) References Cited

U.S. PATENT DOCUMENTS 5,917,056 A  6/1999  Bombardelli

FOREIGN PATENT DOCUMENTS

WO   WO 01/02407   1/2001

OTHER PUBLICATIONS

Tetrahedron Letters, Robert Holton et al, "Selective Protection of the C(7) and C(10) Hydroxyl Groups in 10–Deacetyl Baccatin III", 1998, pp. 2883–2886.

*Primary Examiner*—Taofiq Solola
(74) *Attorney, Agent, or Firm*—Young & Thomspon

(57) ABSTRACT

A process for the preparation of the compound 13-(N-Boc-β-isobutylisoserinyl)-14β-hydroxybaccatine III 1,14-carbonate.

11 Claims, No Drawings

PROCESS FOR THE PREPARATION OF TAXAN DERIVATIVES

The present invention relates to a process for the preparation of the compound 13-(N-Boc-β-isobutylisoserinyl)-14β-hydroxybaccatine III 1,14-carbonate, of formula (I):

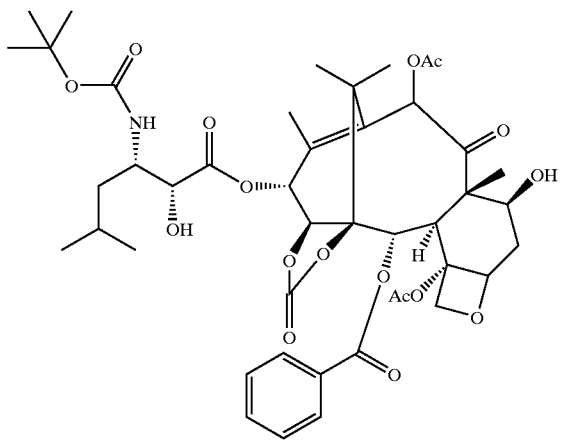

Compound (I), disclosed in PCT WO 01/02407, is particularly active against breast, lung, ovary, colon, prostate, kidney and pancreas tumors, as well as against cells resistant to known antitumor agents, such as adriamycin, vinblastine and some Pt derivatives. 14β-Hydroxy-1,14-carbonate-deacetylbaccatine III derivatives are usually prepared starting from the precursor 14β-hydroxy-deacetylbaccatine III, a natural compound obtainable in small amounts by extraction of *Taxus wallichiana* leaves, as disclosed in EP 559,019. There is strong need for alternative processes for the easy and effective preparation of 14β-hydroxy-1,14-carbonate-deacetylbaccatine III derivatives, in particular of compounds (I).

The process according to the invention uses as starting material 10-deacetylbaccatine III which, contrary to 14β-hydroxy-baccatine III, may be easily recovered in large amounts from *Taxus baccata* leaves.

Therefore, the invention relates to a process for the preparation of the compounds of formula (I) which comprises the following steps:

a) protection of the hydroxyls at the 7- and 10-positions of 10 deacetylbaccatine III:

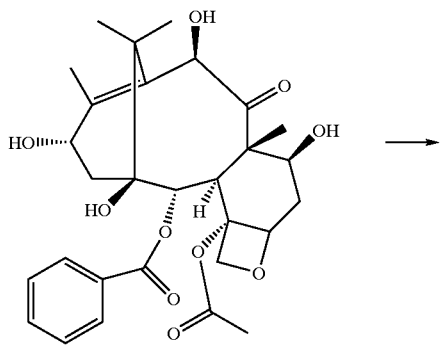

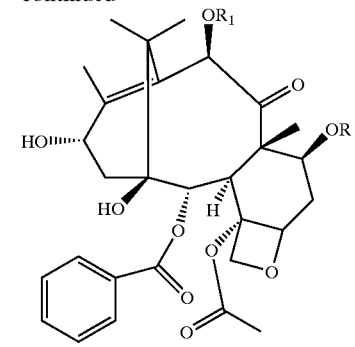

wherein R and $R_1$, which can be the same or different, are selected from hydrogen, $C_1$–$C_{10}$ alkyl or aryl, $C_1$–$C_{10}$ alkyl- or aryl-carbonyl, trichloroacetyl, $C_1$–$C_4$ trialkylsilyl; preferably, when R and $R_1$ are the same, they are trichloroacetyl, whereas when they are different, preferably R is trichloroacetyl and $R_1$ is acetyl, or R is triethyl or trimethylsilyl or BOC and $R_1$ is acetyl;

b) two-step oxidation to give the derivative oxidized to carbonyl at the 13-position and hydroxylated at the 14-position:

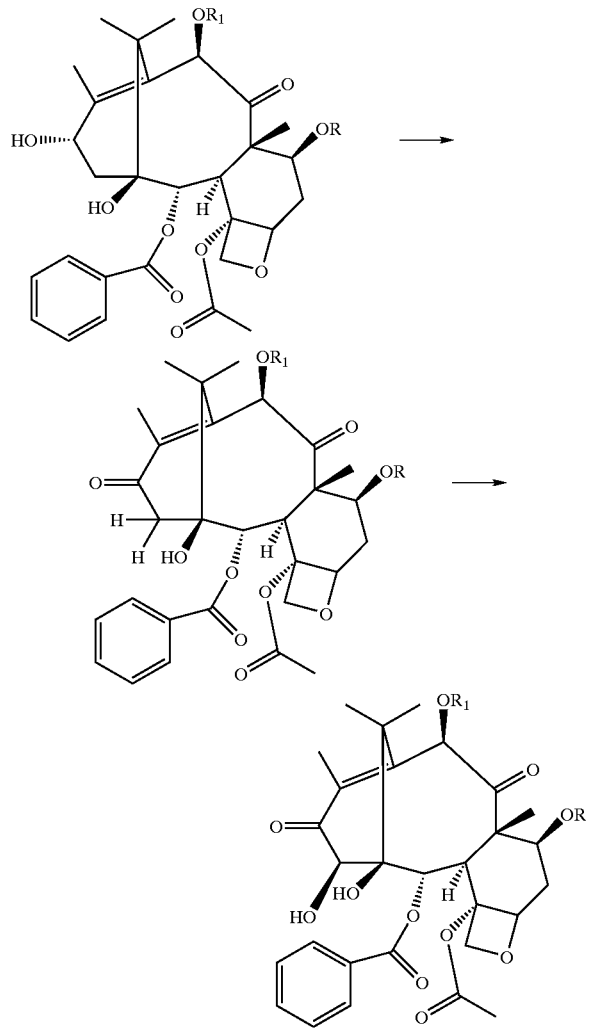

c) carbonation of the vicinal hydroxyls at the 1- and 14 positions to give the 1,14-carbonate derivative:
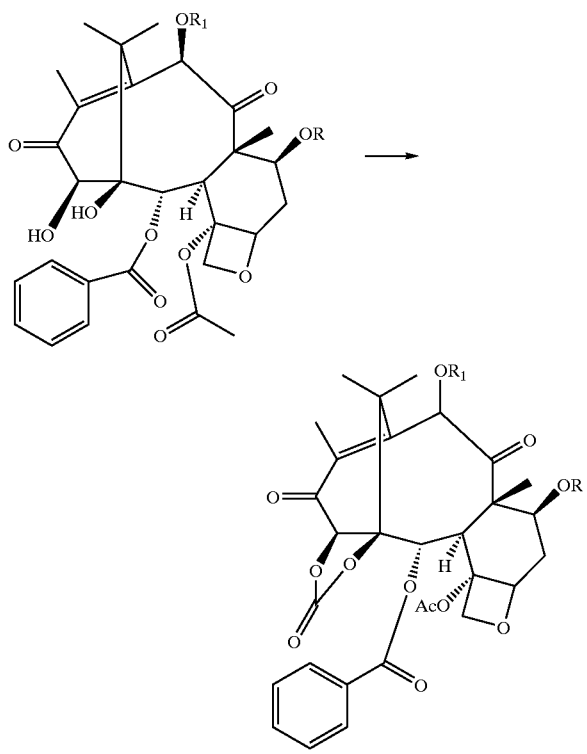
d) reduction of the carbonyl at the 13-position:
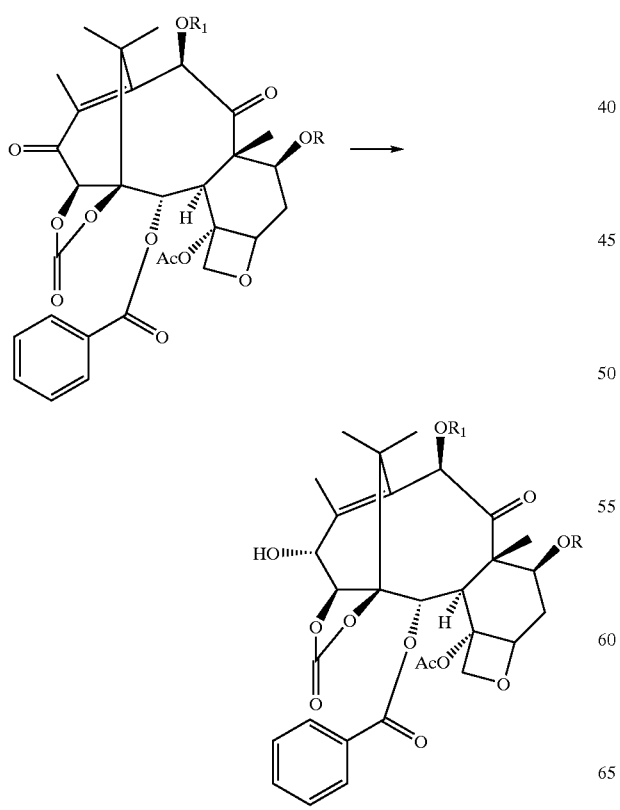
e) removal of the protective groups at the 7- and 10-positions:
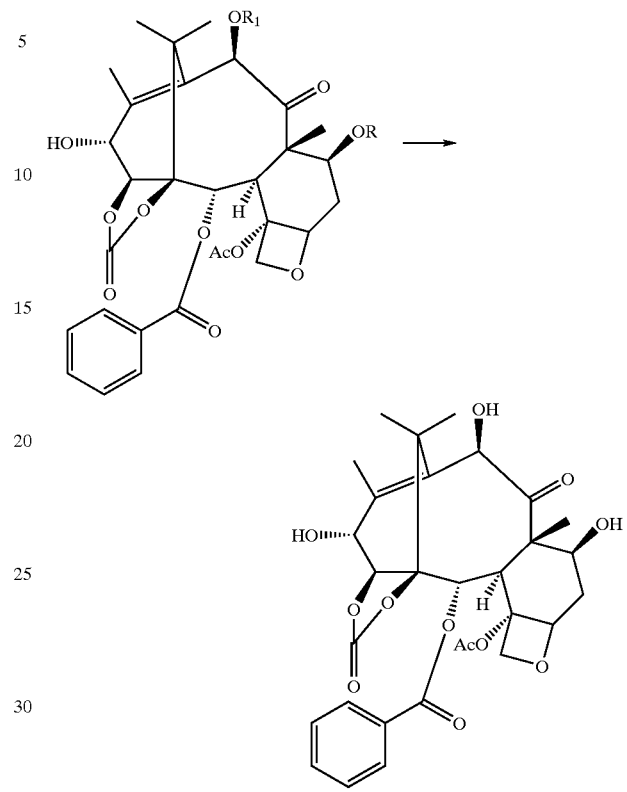
f) selective acetylation of the hydroxyl at the 10-position:
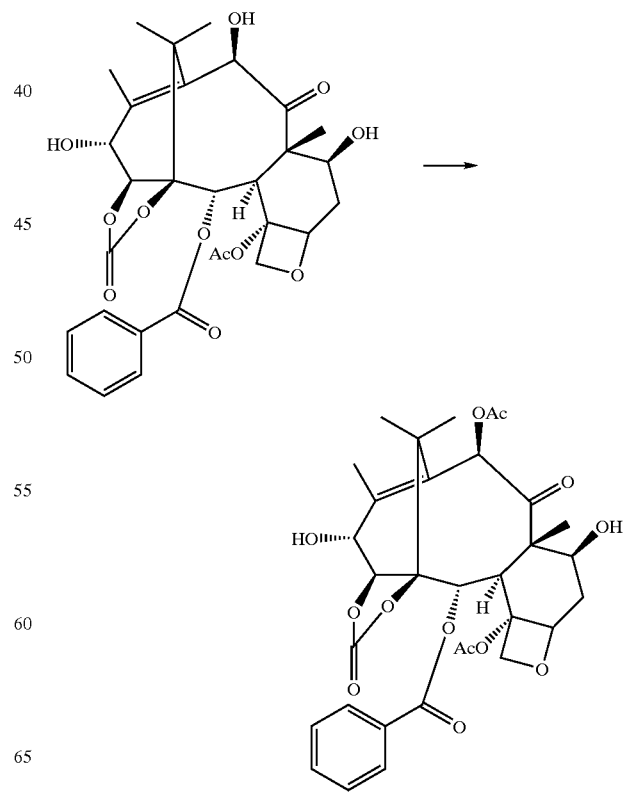

g) transformation 14β-hydroxy-baccatine-1,14-carbonate III into the derivative triethylsilylated at the 7-position:

h) reaction of the compound from step (g) with (4S,5R)-N-Boc-2-(2,4dimethoxyphenyl)4isobutyl-1-oxazolidine-5-carboxylic acid:

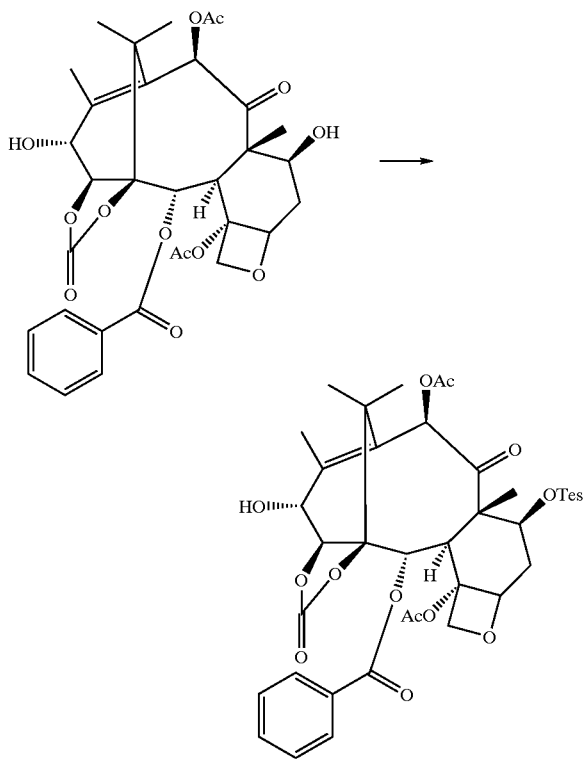

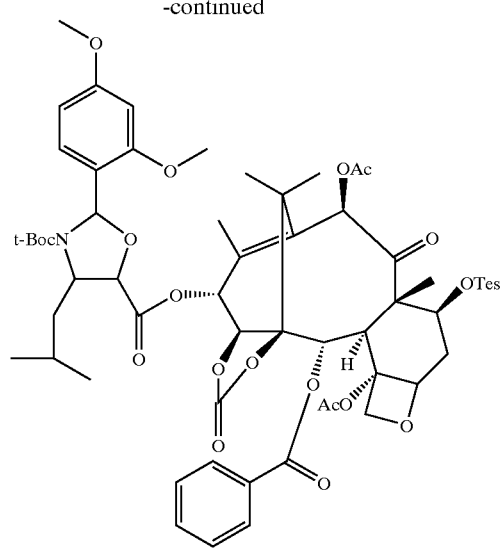

i) removal of the triethylsilyl and dimethoxybenzylidene protective groups from the compound from step (h):

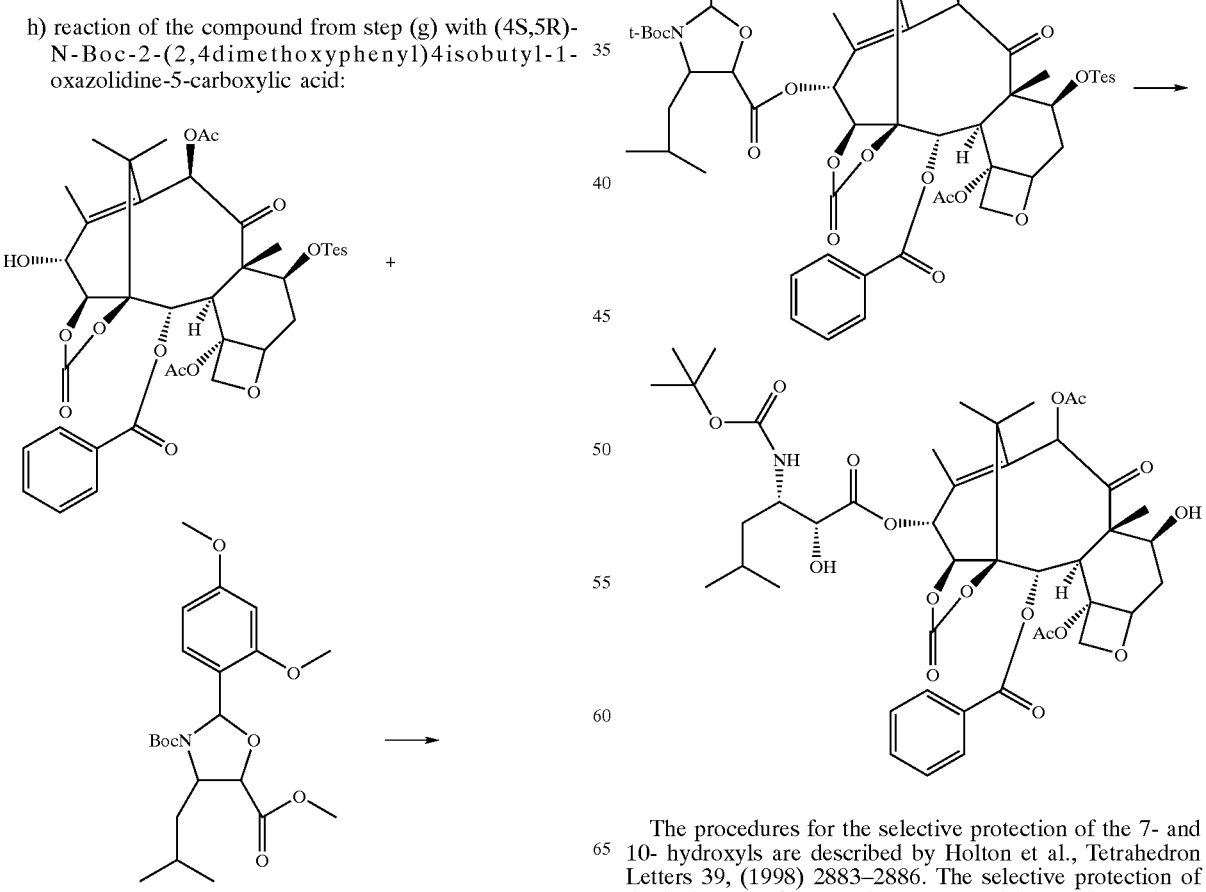

The procedures for the selective protection of the 7- and 10- hydroxyls are described by Holton et al., Tetrahedron Letters 39, (1998) 2883–2886. The selective protection of the hydroxyls of the starting compound deacetylbaccatin III is possible due to their different reactivity. In particular, the reactivity towards acylating, alkylating or silylating agents has been found to vary in the order C(7)—OH>C(10)—OH>C(13)—OH>C(1)—OH, therefore the: groups at 7and 10- can be selectively protected while keeping the hydroxyls at 1- and 13- free. Furthermore, by changing the reaction conditions, it is possible to reverse the reactivity order of the hydroxyls at 7- and 10- thus allowing the differential substitution thereof. Examples of reactants and reaction conditions usable in the protection of the hydroxyls at 10- and 7- are reported in the above cited publication. Similar selectivities are obtained starting:from 14β-bydroxybaccatine-1,14-carbonate.

According to a preferred embodiment, deacetylbaccatine III is reacted with trichloroacetyl chloride in methylene chloride in the presence o triethylamine and using dimethylaminopyridine (DMAP) in catalytic amounts. The use of the protective trichloroacetyl groups proved to be very advantageous in the subsequent oxidation, carbonation and reduction steps (respectively (b), (c) and (d)). In particular the 7,10-bis-trichloroacetate derivative, which is obtained in quantitative yields from the starting product, is oxidized and carbonated, then easily reduced at the 13-position with simultaneous deprotection of the trichloroacetic groups to give 14-hydroxy-1,14 carbonate-deacetylbaccatine III. The use of DMAP in catalytic amounts provides obvious advantages from the industrial and environmental point of views, considering that acylations of this substrate have up to now been carried out in pyridine, which involves problems of disposing of the residual solvent.

The oxidation step (b) of the hydroxyl at the 13-position is carried out with manganese dioxide or bismuth dioxide or ozone in a solvent selected from acetonitrile, acetone or ethyl acetate/methylene chloride 9:1 mixtures, under vigorous stirring, preferably with ozone or manganese dioxide in acetonitrile or acetone. The reaction with ozone rapidly forms the derivative oxidised at the 13-position, while with $MnO_2$ the reaction proceeds quickly to give the derivative oxidized at the 13-position which can be recovered from the reaction medium, whereas a longer reaction yields the 13- oxidised and 14- hydroxylated derivative.

The subsequent carbonation step (c) of the hydroxyls at the 1- and 14-positions is usually effected with phosgene or in a methylene chloride/toluene mixture in the presence of pyridine. Subsequently, the resulting 1,14-carbonate derivative can be easily reduced at the 13-position to give the corresponding 13-hydroxy derivative (step (d)). Said reduction takes place regioselectively at the carbonyl at 13-, while the carbonyl at 9- remains unchanged. This reaction is usually carried out with sodium borohydride in methanol or tetrabutylammonium borohydride and provides high yields. The subsequent step (e) consists in deprotecting the hydroxyls at the 7- and 10-positions to give 14β-hydroxy-1,14-carbonate deacetylbaccatin III. The conditions and the reactants which can be used in the selective deprotection of the hydroxyls at 7- and 10- are described in Zheng et al., Tetrahedron Lett., 1995, 36, 2001, and in Datta et al., J. Org. Chem., 1995, 60. 761.

The selective acetylation at the 10-position (step (f)) is carried out with acetic anhydride in the presence of cerium, scandium, or ytterbium salts, preferably $CeCl_3.7H_2O$. Afterwards, the hydroxyl at the 7-position is protected by silylation (step (g)). The subsequent step (h) involves the condensation between 14β-hydroxy-7-Tes- 1,14-carbonate-baccatine III and (4S,5R)N-Boc-2-(2,4-dimethoxyphenyl)-4-isobutyl-1-oxazolidine-5-carboxylic acid. The latter is prepared as described in PCT WO 01/02407. The reaction is carried out in dry apolar organic solvents, in the presence of a base and of a condensation agent such as dicyclohexyl-carbodiimide (DCC).

Finally, in step (i), the triethylsilyl group can be removed with pyridinium fluoride in acetonitrile/pyridine solution under nitrogen, whereas the dimethoxybenzylidene group can be removed in methylene chloride by addition of methanol HCl and subsequently of $NaHCO_3$.

The following examples illustrate the invention in greater detail.

EXAMPLE I

Preparation of 7,10-Bistrichloroacetyl-10-desacetylbaccatine III $1^{st}$ Alternative:

4.77 ml of trichloroacetic anhydride (42.32 mmoles) were dropped into a solution of 10 g of 10-deacetylbaccatine III (18.4 mmoles) in 125 ml of dry methylene chloride and 42 ml of pyridine. The reaction mixture was kept under stirring for three hours or otherwise until completion of the reaction, which was monitored by TLC on silica gel using a n-hexane/ethyl acetate 1:1 mixture as eluent. Upon completion of the reaction, 5 ml of methanol were added to destroy the trichloroacetic anhydride excess and then water was added. The organic phase was thoroughly washed with water acidified with HCl to remove pyridine, while the residual organic phase was dried over $MgSO_4$ and concentrated to dryness under vacuum, to obtain a pale yellow solid (17 g) which after crystallization from chloroform has: $[\alpha]_D$-34°($CH_2Cl_2$ C5.8) IR (KBr) 3517, 1771, 1728, 1240. 981, 819, 787, 675 $cm^{-1}$;

$^1$H-NMR (200MH): δ 8.11 (Bz C), 7.46 (Bz, BB'), 6.50 (s, H-10), 5.72 (m, H-7 H-29), 5.02 (d, J=8 Hz, H-5), 4.95 (8m, H-13), 4.37 (d, J=8 Hz, H-20a), 4.18 (d, J=8 Hz, H-20b), 4.02 (d, J=6 Hz, H-3), 2.32 (s, 4-Ac), 2.22 (s, H-18), 1.91 (s, H-19), 1.25 and 1.11 (s, H-16, H-17), 1.94 (m, H14α), 1.89 (m, H14β).

$2^{nd}$ Alternative:

10-DAB III (10 g, 18.38 mmol) was suspended in $CH_2Cl_2$ (120 ml), DMAP (220 mg, 1.4 mmol, 0.1 eqv.) was added and the mixture was cooled to 0° C. on ice bath. Then $Et_3N$ (10.26 ml, 73.6 mmol, 4 eqv.) and, immediately after, $Cl_3COCl$ (4.12 ml, 36.8 mmol, 2 eqv.) were added under nitrogen stream in 5 min. keeping temperature below 10° C. After completion of the addition, the mixture was left under stirring on ice bath for 15 min, then the bath was removed and the mixture was stirred at r.t. for 1 h. After 1 h the reaction was monitored by TLC (AcOEt 2/n-hexane 3, Rf 10-DAB III=0.05, Rf 7,10-bistrichloroacetyl-10-DAB III= 0.26) and $Cl_3CCOCl$ (1 ml, 0.5 eqv.) was added. Stirring was maintained at r.t. for 10 min, then the mixture was poured into a beaker containing 160 g of triturated ice, stirring at r.t. until equilibrium (approx. 1 h). After that, the aqueous phase was separated and extracted with $CH_2Cl_2$ (3×40 ml). The combined organic phases were washed with 1N HCl (20 ml), then with a $NaHCO_3$ saturated solution (20 ml), dried over $Na_2SO_4$ and the solvent was evaporated off. Crude weight: 16.5 g. After crystallization from chloroform, IR, $^1$H-NMR and $[\alpha]_D$ spectra were consistent with those of the compound obtained using pyridine and trichloroacetic anhydride.

EXAMPLE II

Oxidation at 13- and Hydroxylation at 14- of 10-deacetylbaccatine III 7,10-bistrichloroacetate To a solution of 10-deacetylbaccatine III 7,10-bistrichloroacetate (3 g) in acetonitrile (40 ml), 30 g of activated MnO$_2$ were added and the suspension was magnetically stirred at room temperature and monitored by TLC (petroleum ether-ethyl acetate 5:5; Rf starting material approx; 0.31). After about one hour, the formation of the 13-dehydroderivative is complete (TLC analysis, Rf of the 13-dehydroderivative about 0.50). Stirring was then kept for about 72 hours, during which the 13-dehydroderivative was slowly oxidized to its 14β-hydroxy derivative (Rf about 0.36). The reaction mixture was filtered through Celite, and the cake was repeatedly washed with ethyl acetate. The solvent was evaporated off and the residue was purified by column chromatography on silica gel (100 ml, eluent petroleum ether-ethyl acetate 7:3) to afford 170 mg of the 13-dehydroderivative and 1,05 g of the 14β-hydroxy-13-dehydroderivative.

13-Dehydro-14β-hydroxy-10-deacetylbaccatin III, 7,10-bis trichloroacetate: white powder, mp 97° C.; IR (KBr disc): 3440, 1780, 1767, 1736, 1686, 1267, 1232, 1103, 1010, 854 cm$^{-1}$;

$^1$H-NMR (200MHz, CDCl$_3$): δ 8.07 (Bz AA'), 7.60 (Bz, C), 7.49 (Bz, BB'), 6.52 (s, H-10), 5.92 (d, J=6.7 Hz, H-2), 5.70 (br t, J=8.0 Hz, H-7), 4.95 (br d, J=8.2 Hz, H-5), 4.37 (d, J=8.2 Hz, H-20a), 4.31 (d, J=8.2 Hz, H-20b), 4.17 (s, H14), 4.02 (d, J=6.7 Hz, H-3), 2.71 (m, H-6), 2.29 (s, OAc), 2.17 (s, OAc), 1.96 (s, H-18), 1.27, 1.01 (s, H-16, H-17 and H-19).

EXAMPLE III

Oxidation at 13- and Hydroxylation at 14- of 7-triethylsilylbaccatin III

To a solution of 7-triethylsilylbaccatin III (1.0 g) in acetonitrile (10 ml), 10 g of activated MnO$_2$ were added and the suspension was magnetically stirred at room temperature and monitored by TLC (petroleum ether-ethyl acetate 6:4; Rf starting material approx. 0.25). After about 2 hours, formation of the 13-dehydroderivative was complete (TLC analysis, Rf 13-dehydroderivative about 0.45). Stirring was continued for approx. 188 hours, during which additional MnO$_2$ (10 g) was added. The 13-dehydroderivative was slowly oxidized to its 14β-hydroxy derivative (Rf about 0.38). The reaction mixture was filtered through Celite and the cake was washed with ethyl acetate. The solvent was evaporated off and the residue was purified by column chromatography on silica gel (40 ml, eluent petroleum ether-ethyl acetate 7:3) to afford 126 mg of the 13-dehydroderivative, 479 mg (46%) of 14β-hydroxy-13-dehydroderivative and 189 mg of a mixture thereof.

13-Dehydro-7-triethylsilylbaccatin III. White powder, mp 168° C. [α]$_D^{25}$-35 (CH$_2$Cl$_2$, C 0.67) IR (KBr) 3488, 1726, 1711, 1676, 1373, 1269, 1244, 1230, 1105 cm$^{-1}$; $^1$H-NMR (200MH CDCl$_3$): δ 8.07 (Bz AA'), 7.60 (Bz, C), 7.49 (Bz, BB'), 6.59 (s, H-10), 5.69 (d, J=6.9 Hz, H-2), 4.92 (d, J=8.2 Hz, H-5), 4.48 (dd, J=10.6 Hz, H-7), 4.33 (d, J=8.0 Hz, H-20a), 4.12(d, J=8.0 Hz, H-20b), 3.91, (d, J=6.9 Hz, H-3), 2.96 (d, J=20 Hz, H-14a), 2.65 (d, J=20 Hz, H-20b), 2.50 (m, H-6α), 2.23 (s, OAc), 2.19 (s, OAc+H-18), 1.67, 1.28, 1.19 (s, H-16, H-17 and H-19), 0.19 (m, TES).

13-Dehydro-14β-hydroxy-10-deacetylbaccatin III, 7,10-bis trichloroacetate: white powder, mp 153° C. [α]$_D^{25}$+20 (CH$_2$Cl$_2$, C 0.75) IR (KBr) 3431, 1723, 1692, 1371, 1269, 1242, 1223, 1096 cm$^{-1}$; $^1$H-NMR (500 MH CDCl$_3$): δ 8.06 (Bz AA'), 7.60 (Bz, C), 7.48 (Bz, BB'), 6.51 (s, H-10), 5.88 (d, J=6.9 Hz, H-2), 4.90 (d, J=8.2 Hz, H-5), 4.47 (dd, J=10.6 7 Hz, H-7), 4.30 (d, J=8 Hz, H-20a), 4.28 (d, J=8.2 Hz, H-20b), 4.13 (br d, J=2 Hz, H-14), 3.84 (d, J=6.9 Hz, H-3), 3.69 (br d, J=2 Hz, 14—OH), 3.62 (s, 1-OH), 2.52 (m, H-6α), 2.24 (s, OAc), 2.21 (s, OAc), 2.11 (s, H-18), 1.92(m, H-6β), 1.74, 1.56, 1.28 (s, -h-16, H-17 and H-19), 0.94 (m, TES), 0.59 (m, TES). HRNS: 714.3092 (calculated for C$_{37}$H$_{50}$O$_{12}$Si 714.3092).

EXAMPLE IV

Preparation of 1,14-Carbonate-13-dehydro-7-TES-14β-hydroxy-baccatine III

To a solution of phosgene (1.8 ml of a 20% solution in toluene, 3.4 mmol, 20 mol. equiv.) and pyridine (0.56 ml, 6,8 mmol, 20 mol. equiv.) in CH$_2$Cl$_2$ (2 ml), a solution of 13-dehydro-14β-hydroxy-7-triethylsilylbaccatin III (124 mg, 1,17 mmol) in CH$_2$Cl$_2$ (1 ml) was added dropwise in 5 min. The mixture was stirred at room temperature for 1 hour, subsequently quenching the excess phosgene by addition of a NaHCO$_3$ saturated solution and extraction with CH$_2$Cl$_2$. The organic phase was washed with a NaHCO$_3$ saturated solution, brine, and dried (Na$_2$SO$_4$). The solvent was evaporated off to yield a reddish residue, which was purified on a short silica gel column (about 5 ml, eluent hexane/ethyl acetate 8:2) to afford 118 mg (92%) of the carbonate. If the reaction is carried out using with triethylamine as the base and without inverse addition, an about 1:15 mixture of 1,14-cabonate and 2-debenzoyl-1,2-carbonate-14 benzoate is obtained.

13-Dehydro-14β-hydroxy-7-triethylsilylbaccatin III 1,14-carbonate. White powder, mp 153° C. [α]$_D^{25}$+23 (CH$_2$Cl$_2$, C 0.75) IR (KBr) No. of OH band 1834, 1734, 1709, 1373, 1242, 1225, 1088, 1057 cm$^{-1}$; $^1$H-NMR (200 MH CDCl$_3$): β 7.99 (Bz AA'), 7.60 (Bz, C), 7.48 (Bz, BB'), 6.51 (s, H-10), 6.12 (d, J=6.9 Hz, H-2), 4.90 (d, J=8.2 Hz, H-5), 4.78 (s, H-14), 4.44 (dd, J=10.7 Hz, H-7), 4.34 (d, J=8 Hz, H-20a), 4.19 (d, J=8.2 Hz, H-20b), 3.80 (d, J=6.9 Hz, H-3), 2.50 (m, H-6α), 2.23 (s, OAc), 2.22 (s, OAc), 2.19 (s, H-18), 1.92 (m, H-6β), 1.72, 1.39, 1.26 (s, -H-16, H-17 and H-19), 0.90 (m, TES), 0.56 (m, TES). HRNS: 740.2851 (calculated for C$_{38}$H$_{48}$O$_{13}$Si 740.2864).

13-Dehydro-14β-hydroxybaccatine III 1,14-carbonate. White powder 240° C. [α]$_D^{25}$-2.5 (CH$_2$Cl$_2$, C 0.4) IR (KBr) 3539, 1831, 1736, 1240, 1088, 1068, 1057, 1024 cm$^{-1}$; $^1$H-NMR (200 MH CDCl$_3$): δ 7.98 (Bz AA'), 7.61 (Bz, C), 7.50 (Bz, BB'), 6.39 (s, H-10), 6.14 (d, J=6.9 Hz, H-2), 4.98 (d, J=8.2 Hz, H-5), 4.80 (s, H-14), 4.43 (dd, J=10.7 Hz, H-7), 4.35 (d, J=8 Hz, H-20a), 4.24 (d, J=8.2 Hz, H-20b), 3.80 (d, J=6.9 Hz, H-3), 2.50 (m, H-6α), 2.30 (s, OAc), 2.20 (s, OAc), 2.15 (s, H-18), 1.90 (m, H-6β), 1.74, 1.34, 1.25 (s, H-16, H-17 and H-19), HRMS: 626.2005 (calculated for C$_{33}$H$_{34}$O$_1$ 626.1999).

EXAMPLE V

Preparation of 1,14-Carbonate-7-O-triethylsilyl Baccatine III

To a solution of 13-dehydro-14β-hydroxy-7-triethylsilylbaccatin III 1,14-carbonate (50 mg) in methanol (5 ml), an excess NaBH$_4$ (about 20 mg) was added in small portions. After 30 min, the reaction mixture was added with saturated NH$_4$Cl, extracted with ethyl acetate, washed with brine and dried over Na$_2$SO$_4$. The solvent was evaporated off and the residue was purified by column chromatography on silica gel (about 5 ml, elution with hexane-ethyl acetate 8:2) to afford 35 mg of the 13α-hydroxy derivative and 9 mg of the 13p-hydroxy derivative.

14β-Hydroxy-7-triethylsilylbaccatin III 1,14-carbonate [α]$_D^{25}$-35 (CH$_2$Cl$_2$, C 0.60) IR (KBr) 3054, 1819, 1736, 1603, 1371, 1261, 1238, 1090, 1069, cm$^{-1}$; $^1$H-NMR (200 MH CDCl$_3$): δ 8.06 (Bz AA'), 7.65 (Bz, C), 7.50 (Bz, BB'), 6.47 (s, H-10), 6.12 (d, J=6.9 Hz, H-2), 5.05 (br d, J=5.5 Hz, H-13), 4.98 (br d, J=9 Hz, H-5), 4.83 (d, J=5 Hz, H-14), 4.50 (dd, J=10.7 Hz, H-7), 4.34 (d, J=8 Hz, H-20a), 4.23 (d, J=8 Hz, H-20b), 3.75 (d, J=6.9 Hz, H-3), 2.56 (m, H-6α), 2.34 (s, OAc), 2.22 (s, OAc), 1.78 (m, H-6β), 1.35 (s, H-18), 1.75, 1.18, 0.95 (s, -H-16, H-17 and H-19), 0.90 (m, TES), 0.62 (m, TES).

14 β-Hydroxy-7-triethylsilyl-13-epibaccatine III 1,14-carbonate. Amorphous, $[α]_D^{25}$–13 (CH$_2$Cl$_2$, C 0.60) IR (KBr) 3630, 1825, 1734, 1603, 1375, 1262, 1091, 1071, 1049 cm$^{-1}$; $^1$H-NMR (200 MH CDCl$_3$): δ 8.01 (Bz AA'), 7.63 (Bz, C), 7.48 (Bz, BB'), 6.44 (s, H-10), 6.12 (d, J=7.2 Hz, H-2), 4.90 (br d, J=9 Hz, H-5), 4.81 (d, J=8 Hz, H-14), 4.48 (br, J=8, H-13), 4.50 (dd, J=10. 7 Hz, H-7),. 4.41 (d, J=8 Hz, H-20a), 4.31 (d, J=8 Hz, H-20b), 3.68 (d, J=7.2 Hz, H-3), 2.60 (m, H-6α), 2.32 (s, OAc), 2.26 (s, H-18), 2.21 (s, OAc), 1.80 (m, H-6β), 1.72, 1.43, 1.27 (s, -H-16, H-17 and H-19), 0.93 (m, TES), 0.61 (m, TES).

EXAMPLE VI

Preparation of 13-Dehydro-14β-hydroxy-7,10-bistrichloroacetyl-baccatine III 1,14-carbonate A solution of 13-dehydro-14β-hydroxy-7,10-bistrichloroacetyl-baccatine III (200 mg) in CH$_2$Cl$_2$ (2 ml) was added in 5 min to a solution of phosgene (20% in toluene, 3.6 ml, 20 equiv.) and pyridine (1.12 ml, 20 equiv.) in CH$_2$Cl$_2$ (2 ml). The mixture was stirred at r.t. for 1 h, then the excess phosgene was quenched with a NaHCO$_3$ saturated solution (3 ml). The mixture was extracted with CH$_2$Cl$_2$, the organic portion was washed with a NaHCO$_3$ saturated solution, then with a NaCl saturated solution and dried over Na$_2$SO$_4$. The solvent was evaporated off and the residue was purified by column chromatography on silica gel (eluent hexane/AcOEt 9:1) to afford 175 mg (89%) of the carbonate.

13-Dehydro-14β-hydroxy-7,10-bistrichloroacetyl-baccatine III 1,14-carbonate. White amorphous solid. IR (KBr) 1834, 1771, 1735, 1709, 1232, 1103, 1010, 854 cm$^{-1}$.

$^1$H-NMR (200 MHz, CDCl$_3$): δ=8.03 (Bz AA'), 7.60 (Bz, C), 7.50 (Bz, BB'), 6.52 (s, H-10), 5.92 (d, J=6.7 Hz, H-2), 5.70 (br t, J=8.0 Hz, H-7), 4.95 (br d, J=8.2 Hz, H-20b), 4.77 (s, H-14), 4.02 (d, J=6.7 Hz, H-3), 2.71 (m, H-6), 2.29 (s, OAc), 1.96 (s, H-18), 1.27–1.01 (m, H-16, H-17, H-19).

EXAMPLE VII

Preparation of 14β-Hydroxy-10-deacetylbaccatine III 1,14-carbonate

A solution of 13-dehydro-14β-hydroxy-7,10-bistrichloroacetyl-baccatine III 1,14-carbonate (500 mg) in MeOH (8 ml) was cooled to 0° C. on ice bath and solid NaBH$_4$ (44 mg) was added thereto in 5 min. The mixture was stirred at r.t. for 1 h, then cooled to 0° C., added with acetone (2 ml) in 5 min and concentrated under mild vacuum, then added with AcOEt (10 ml) and filtered through Celite. The clear solution was washed with a NaCl saturated solution and dried over Na$_2$SO$_4$. The solvent was evaporated off, the residue (4.5:1 mixture of C13 epimers) was purified by chromatography on a silica gel column (eluent hexane/AcOEt 1:1) to afford 251 mg of the title compound and 55 mg of the 13-epimer (88% total) of the deprotected carbonate.

14β-Hydroxy-10-deacetylbaccatine III 1,14-carbonate. White amorphous solid. IR (KBr): 3520 (OH), 1834, 1709, 1232, 1103, 1010, 854 cm$^{-1}$.

$^1$H-NMR (200 MHz, CDCl$_3$): δ=8.03(Bz AA'), 7.60 (Bz, C), 7.50 (Bz, BB'), 6.27 (s, H-10), 5.92 (d, J=6.7 Hz, H-2), 4.95 (br d, J=8.2 Hz, H-20b), 4.85 (m, H-13), 4.77 (s, H-14), 4.42 (br t, J=8.0 Hz, H-7), 4.02 (d, J=6.7 Hz, H-3), 2.71 (m, H-6), 2.29 (s, OAc), 1.96 (s, H-18), 1.27 -1.01 (m, H-16, H-17, H-19).

EXAMPLE VIII

Preparation of 13-(N-Boc-β-isobutylserinyl)-14 β-hydroxybaccatine III 1,14-carbonate To a solution of 14β-hydroxy-10-deacetylbaccatin III 1,14-carbonate (126 mg) in 3 ml of dry tetrahydrofuran, 7.5 mg of CeCl$_3$.7H$_2$O and 0.078 ml of acetic anhydride were added. The reaction mixture was kept under stirring at room temperature for 5 h. during which the reaction mixture became homogeneous. 1.5 g of ice were added, keeping stirring for 1 h. The organic solvent was evaporated off under vacuum and the residue was diluted with 5 ml of H$_2$O. The formed precipitate was filtered and dried by suction for 18 h. The resulting product (white powder, 135 mg) has the following characteristics:

$^1$H-NMR (400 MHz, CDCL$_2$). $δ_{ppm}$=1.25, 1.11 (s, H-16 and H-17), 1.66 (s, H-19), 2.04 (s, H-18), 2.22 (s, OAc), 2.29 (s, OAc), 3.89 (d, J=0.9 Hz, H-3), 4.06 (d, J=7 Hz, C20b), 4.20 (d, J=7 Hz, H20a), 4.41 (m, H-7), 4.77 (d, J=4 Hz, H-14), 4.85 (br d, J=4 Hz, H-13), 4.97 (br d, J=8 Hz, H-5), 5.8 (d, J=7 Hz, H-2), 6.31 (s, H-10), 7.44 (t, J (Hz, Bz), 7.55 (d, J=8 Hz, Bz), 8.07 (d, J=8Hz, Bz).

14β-Hydroxybaccatine III 1,14-carbonate (130 mg) was dissolved in dimethylformamide (4 ml) and N-methylimidazole (0.07 ml) was added. Triethylchlorosilane (0.042 ml) was added to the solution under strong stirring at room temperature in 1 h. The mixture was then poured into 10 ml of H$_2$O under strong stirring. The suspension was left at 4° C. for 18 h and the formed white precipitate was filtered off and washed with H$_2$O (5 ml), then with hexane (2×3 ml). The resulting white solid (150 mg) has the same spectroscopical characteristics as those of the compound prepared in Example V.

In a 1l round-bottom flask, 20 g of 14β-hydroxy-7-Tes-1,14-carbonate-baccatine III were placed together with 300 ml of rigorously dry toluene; then 10 g of (4S,5R)-N-Boc-2-(2,4-dimethoxyphenyl)-4-isobutyl-1-oxazolidine-5-carboxylic acid, 2 g of N,N-dimethylaminopyridine (DMAP) and 9.5 g of dicyclohexylcarbodiimide (DCC) dissolved in CH$_2$Cl$_2$ were added. The reaction mixture was refluxed for 3 h, then cooled and the precipitated ureic product was removed. Mother liquors were washed with a NaHCO$_3$ saturated solution to remove the unreacted acid, then with diluted hydrochloric acid to remove DMAP, then again with NaHCO$_3$ to neutrality. The organic phase was concentrated to dryness to obtain 41.5 g of product which can be used as such in the subsequent step.

40 g of this compound were deprotected in two steps, by removing first Tes and then 2,4-dimethoxybenzaldehyde. 40 g of the compound were dissolved in 100 ml of an acetonitrile/pyridine mixture (80:100) under nitrogen and the mixture is cooled to 0° C., then added with 13 ml of pyridinium fluoride and left under stirring for 24 h. The solution was poured into 2l of water and the product was filtered and dried under vacuum.

The residue was dissolved in 60 ml of methylene chloride and this solution was kept under strong stirring at 0° C. and added with 40 ml of 0.6N methanol HCl. The reaction mixture was left under stirring for 2 hr. then diluted with 150 ml of methylene chloride and agitated with a NaHCO3 solution, adjusting pH to 6–7. The organic phase was concentrated to dryness and the residue was crystallized from acetone hexane and dried to obtain 16 g of 13-(N-Boc-β-isobutylisoserinyl)-14β-hydroxybaccatine-1,14-carbonate having the following physico-chemical and spectroscopical characteristics:

| Formula: | $C_{44}H_{57}NO_{17}$ |
| --- | --- |
| Aspect: | white powder. |
| Melting point: | 245° C. |

TABLE 1

Chemical shifts (ppm) $^1$H-NMR in CDCl$_3$ solution (200 MHz)

| H | Ppm, multiplicity (Hz) | H | Ppm, multiplicity (Hz) |
| --- | --- | --- | --- |
| 2 | 6.09-d (7.8) | 2' | 4.30-dd (6.4; 3.2) |
| 3 | 3.68-d (7.4) | 3' | 4.08-m |
| 5 | 4.91-dd (9.7; 2.5) | 4'a | 1.21-m |
| 6α | 2.52-ddd (14.8; 9.8; 6.9) | 4'b | 1.43-m |
| 6β | 1.86-m | 5' | 1.65-m |
| 7 | 4.37-m | 6' | 0.96-d (6.3) |
| 10 | 6.25-s | 7' | 0.95-d (6.3) |
| 13 | 6.44-d (broad, 6.9) | 4-OCOC$\underline{H}_3$ | 2.40-s |
| 14 | 4.84-d (6.9) | 10-OCOC$\underline{H}_3$ | 2.22-s |
| 16 | 1.25-s | Boc | 1.35-s |
| 17 | 1.32-s | o-benzoyl | 8.01-m |
| 18 | 1.87-d (1.6) | m-benzoyl | 7.46-m |
| 19 | 1.69-s | p-benzoyl | 7.58-m |
| 20α | 4.27-d (8.4) | 3'-NH | 4,72-d (9.0) |
| 20β | 4.20-d (8.4) | | |

TABLE 2

Chemical shifts (ppm) $^{13}$C NMR in CDCl$_3$ solution (50.308 MHz)

| C | ppm, multiplicity | C | ppm, multiplicity |
| --- | --- | --- | --- |
| 9 | 201.8-s | 8 | 58.2-s |
| 1' | 172.6-s | 3' | 51.2-d |
| 4-O$\underline{C}$OCH$_3$ | 170.5-s | 3 | 44.6-d |
| 10-O$\underline{C}$OCH$_3$ | 170.2-s | 15 | 41.3-s |
| 2-$\underline{C}$OPh | 164.3-s | 4' | 39.9-t |
| $\underline{C}$=O (Boc) | 155.8-s | 6 | 34.9-t |
| $\underline{C}$=O (carbonate) | 151.4-s | ($\underline{C}$H$_3$)$_3$C Boc | 27.7-q |
| 12 | 139.4-s | 17 | 25.5-q |
| 11 | 133.1-s | 16 | 22.6-q |
| (Me)$_3\underline{C}$(Boc) | 80.0-s | 4-OCO$\underline{C}$H$_3$ | 22.0-q |
| 5 | 83.8-d | 10-OCO$\underline{C}$H$_3$ | 20.2-q |
| 1 | 87.7-s | 5' | 24.3-d |
| 4 | 80.0-s | 6' | 22.7-q |
| 2 | 69.0-d | 7' | 21.6-q |
| 20 | 75.5-t | 18 | 14.6-q |
| 2' | 73.3-d | 19 | 9.8-q |
| 7 | 71.2-d | q-benzoyl | 127.5-s |
| 10 | 74.3-d | o-benzoyl | 129.5-d |
| 13 | 74.1-d | m-benzoyl | 128.6-d |
| 14 | 79.1-d | p-benzoyl | 133.7-d |

Mass spectra: (NH$_{13}$, DEP/CI, positive ions): (m/z) 889 [(MNH$_4$)$^+$], 832 [(MNH$_4$-(CH$_3$)$_3$C)$^+$], 772 [(MNH$_4$-BocNH$_2$)$^+$]

(NH$_3$, DEP/CI, negative ions): (m/z) 871 (M$^-$), 260 (side chain)

Infrared spectrum (KBr pellet): 3521, 3321, 2971, 2953, 1826, 1762, 1706, 1526, 1366, 1238, 1165, 1072, 723 cm$^{-1}$ UV spectrum (MeOH): 231, 276 and 284 nm;

$E_{1\%}$ at 231 nm=180.99

$E_{1\%}$ at 276 nm=14.094

$E_{1\%}$ at 284 nm=12.182

We claim:

1. A process for the preparation of the compound 13-(N-Boc-β-isobutylisoserinyl)-14β-hydroxybaccatine III 1,14-carbonate, of formula (I)

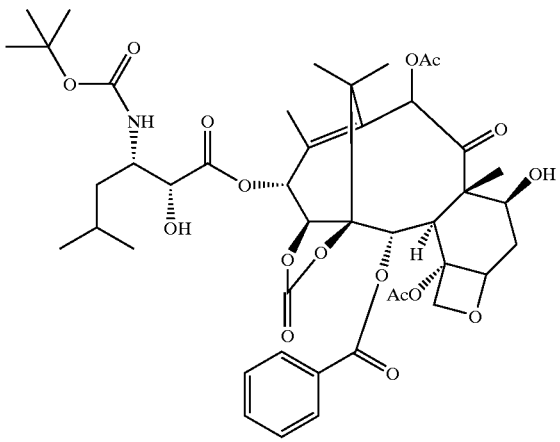

which comprises:

a) protection of the hydroxyls at the 7- and 10-positions of 10 deacetylbaccatine III:

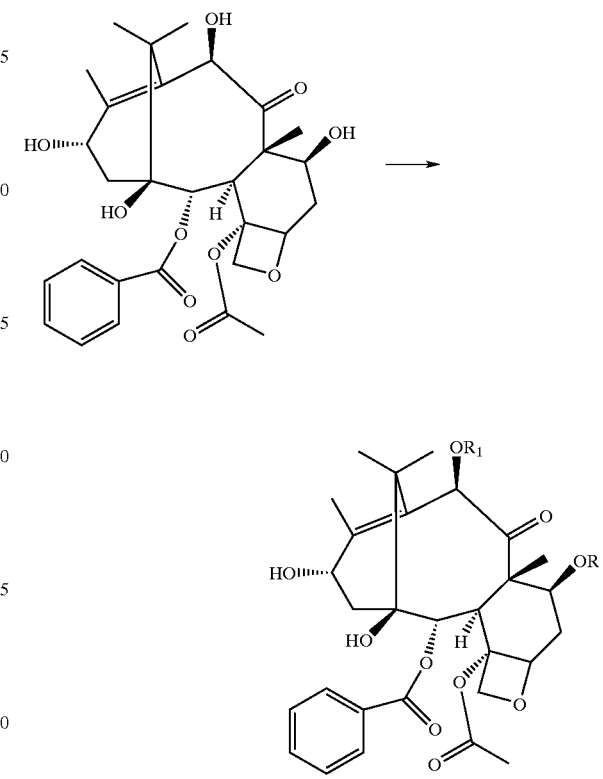

wherein R and R$_1$, which can be the same or different, are selected from hydrogen, $C_1$–$C_{10}$ alkyl or aryl, $C_1$–$C_{10}$ alkyl- or aryl-carbonyl, trichloroacetyl, $C_1$–$C_4$ trialkylsilyl;

b) two-step oxidation to give the derivative oxidized to carbonyl at the 13-position and hydroxylated at the 14-position:
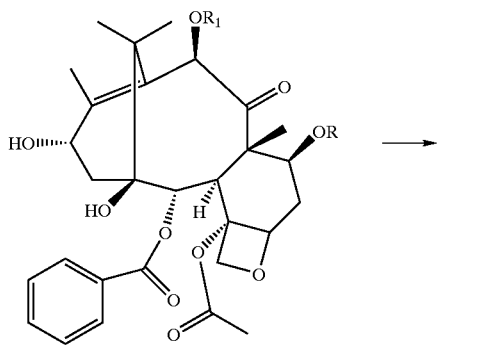
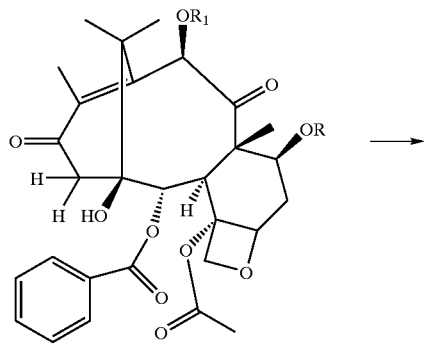
c) carbonation of the vicinal hydroxyls at the 1- and 14-positions to give the 1,14-carbonate derivative:
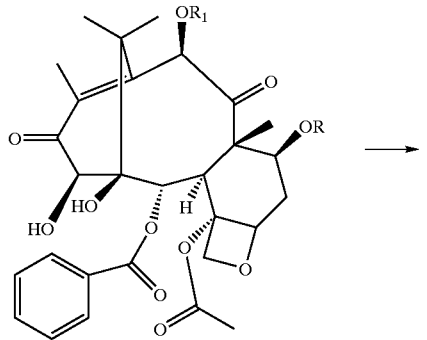
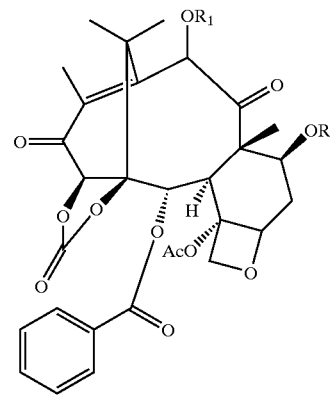
d) reduction of the carbonyl at the 13-position:
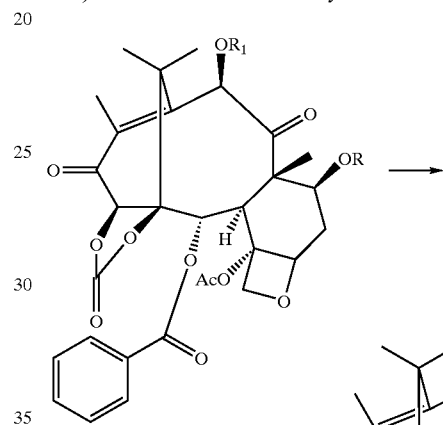
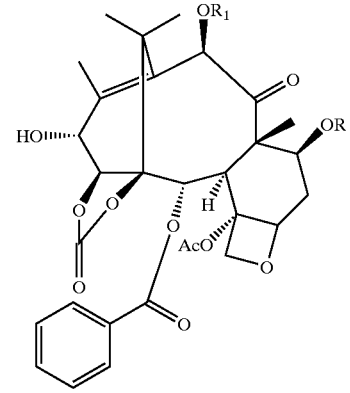
e) removal of the protective groups at the 7- and 10-positions:
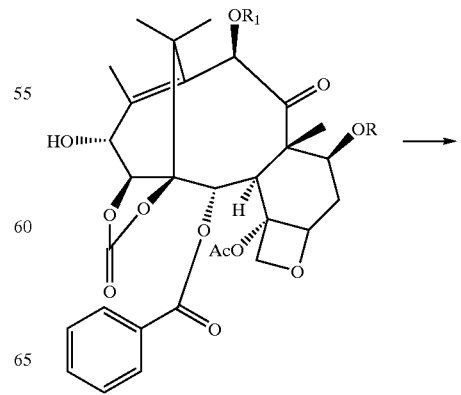

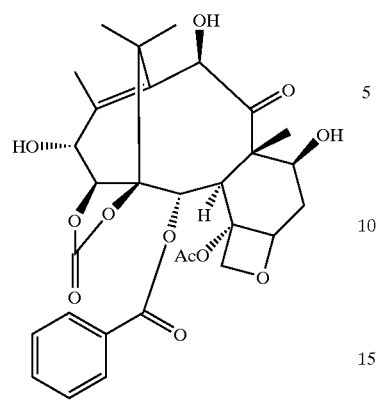
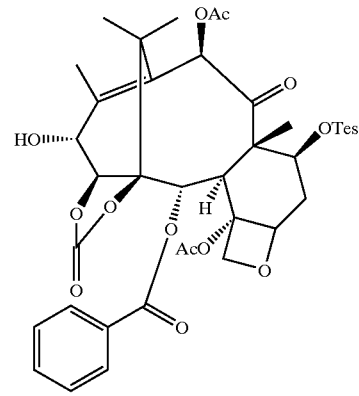
f) selective acetylation of the hydroxyl at the 10-position:
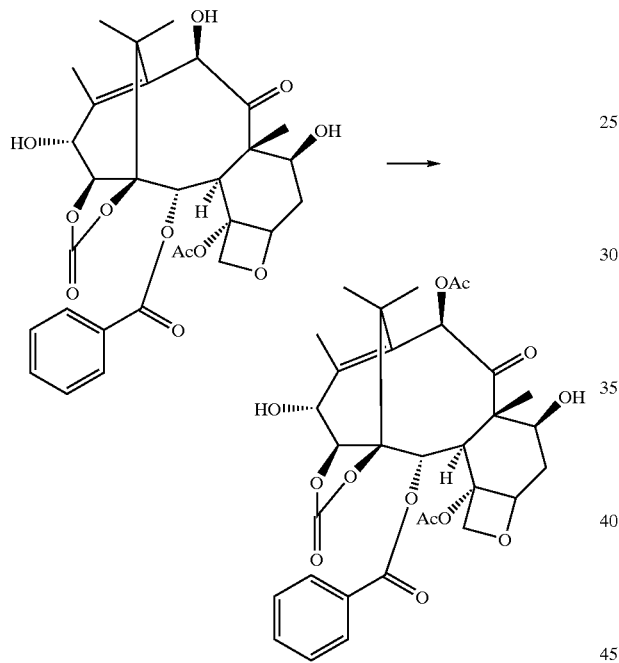
g) transformation of 14β-hydroxy-baccatine-1,14-carbonate III into the derivative triethylsilylated at the 7-position:
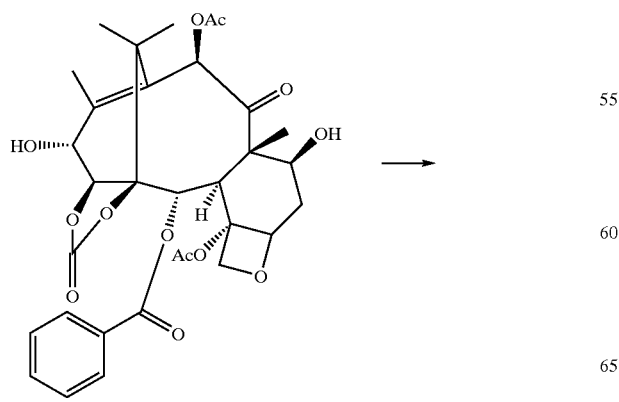
h) reaction of the compound from step (g) with (4S,5R)-N-Boc-2-(2,4-dimethoxyphenyl)4-isobutyl-1-oxazolidine-5-carboxylic acid:
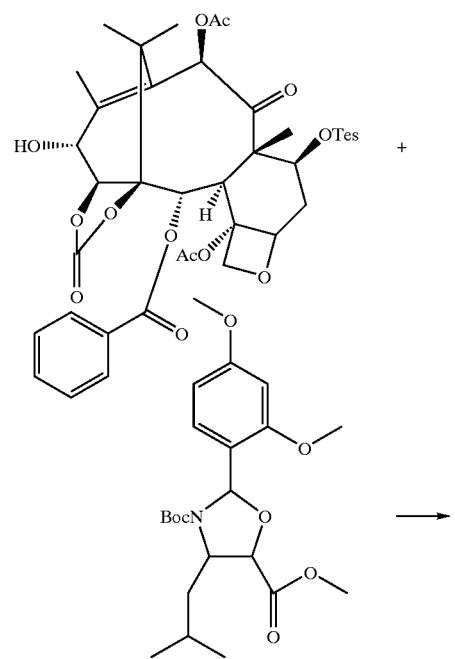
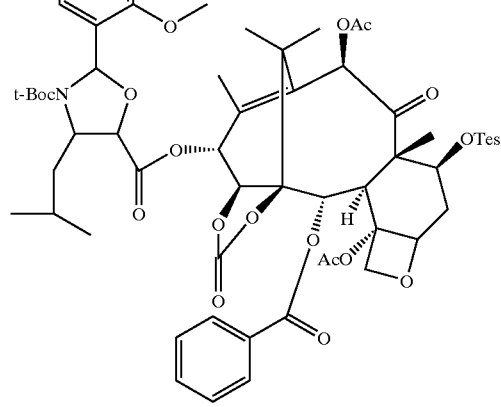

i) removal of the triethylsilyl and dimethoxybenzylidene protective groups from the compound from step (h):

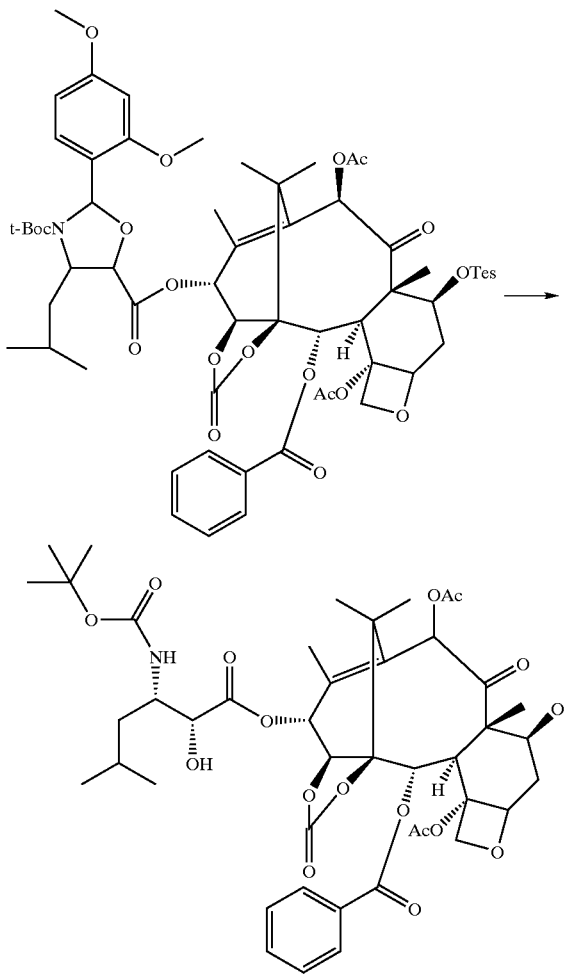

2. A process as claimed in claim 1, wherein R=R$_1$= trichloroacetyl.

3. A process as claimed in claim 1, wherein R and R$_1$ are different and R is trichloroacetyl and R$_1$ acetyl, or R is triethyl or trimethylsilyl and R$_1$ is acetyl.

4. A process as claimed in claim 1, wherein deprotection step (a) of the hydroxyls at the 7- and 10-positions is carried out with trichloroacetyl chloride in methylene chloride in the presence of triethylamine and of catalytic amounts of dimethylaminopyridine.

5. A process as claimed in claim 1, wherein step (b) of oxidation of the hydroxyl at the 13-position and hydroxylation at the 14-position is carried out with manganese dioxide or bismuth dioxide or ozone in a solvent selected from acetonitrile, acetone or an ethyl acetate/methylene chloride mixture.

6. A process as claimed in claim 1, wherein carbonation step (c) of the hydroxyls at the 1- and 14-positions is carried out with phosgene in a methylene chloride/toluene mixture in the presence of pyridine.

7. A process as claimed in claim 1, wherein reduction step (d) to 13-hydroxy is carried out with sodium borohydride in methanol.

8. A process as claimed in claim 1, wherein acetylation step (f) of the hydroxyl at the 10-position is carried out with acetyl chloride.

9. A process as claimed in claim 8, wherein the silylation step (g) is carried out with triethylchlorosilane.

10. A process as claimed in claim 1, wherein the reaction step (h) is carried out in dry apolar organic solvents, in the presence of a base and of the condensation agent dicyclohexylcarbodiimide (DCC).

11. A process as claimed in claim 1, wherein the triethylsilyl protective group is removed in step (i) with pyridinium fluoride in acetonitrile/pyridine solution under nitrogen, and the dimethoxybenzylidene protective group is removed in methylene chloride solvent by addition of methanol HCl and subsequently of NaHCO$_3$.

\* \* \* \* \*